United States Patent

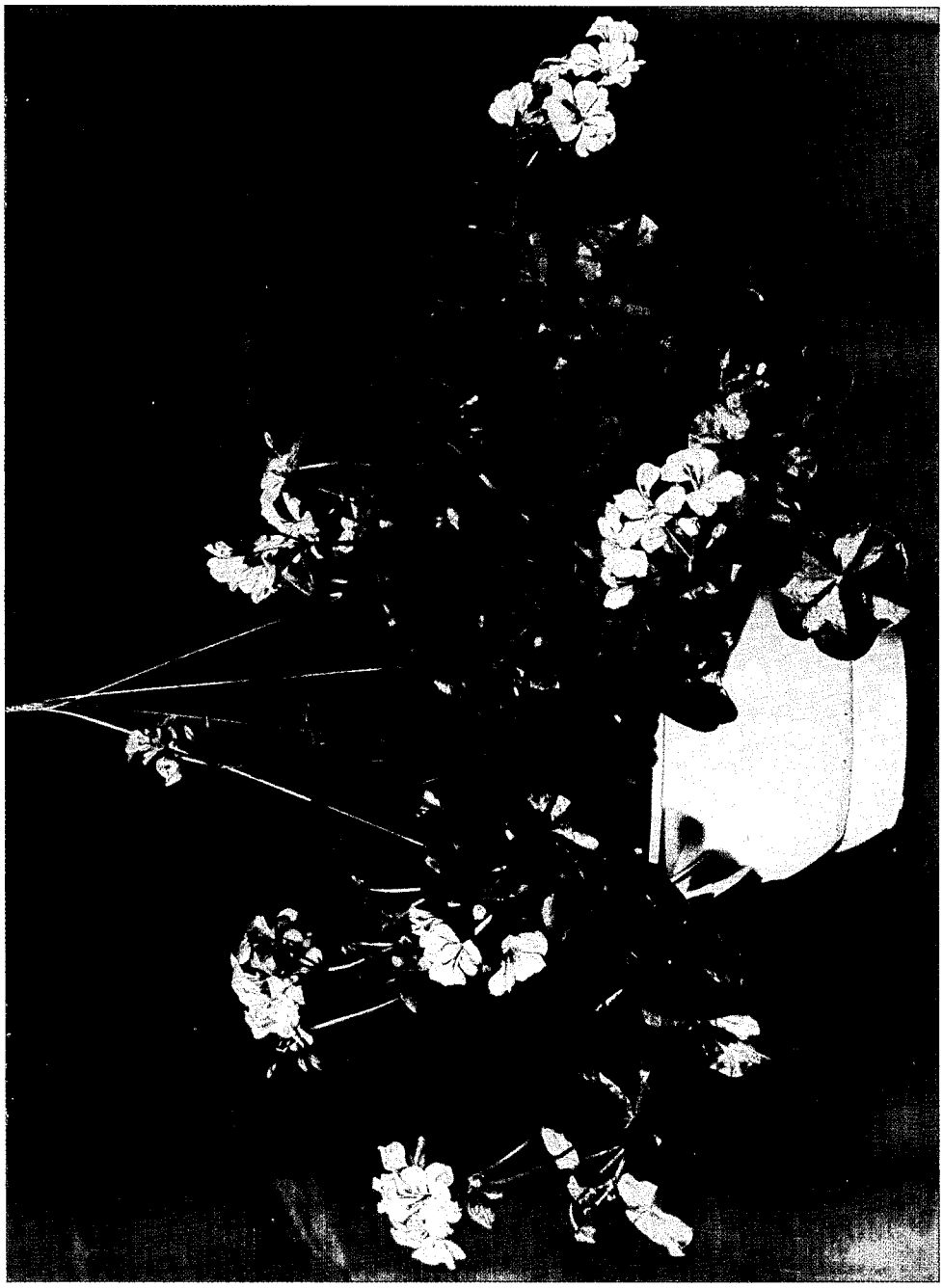

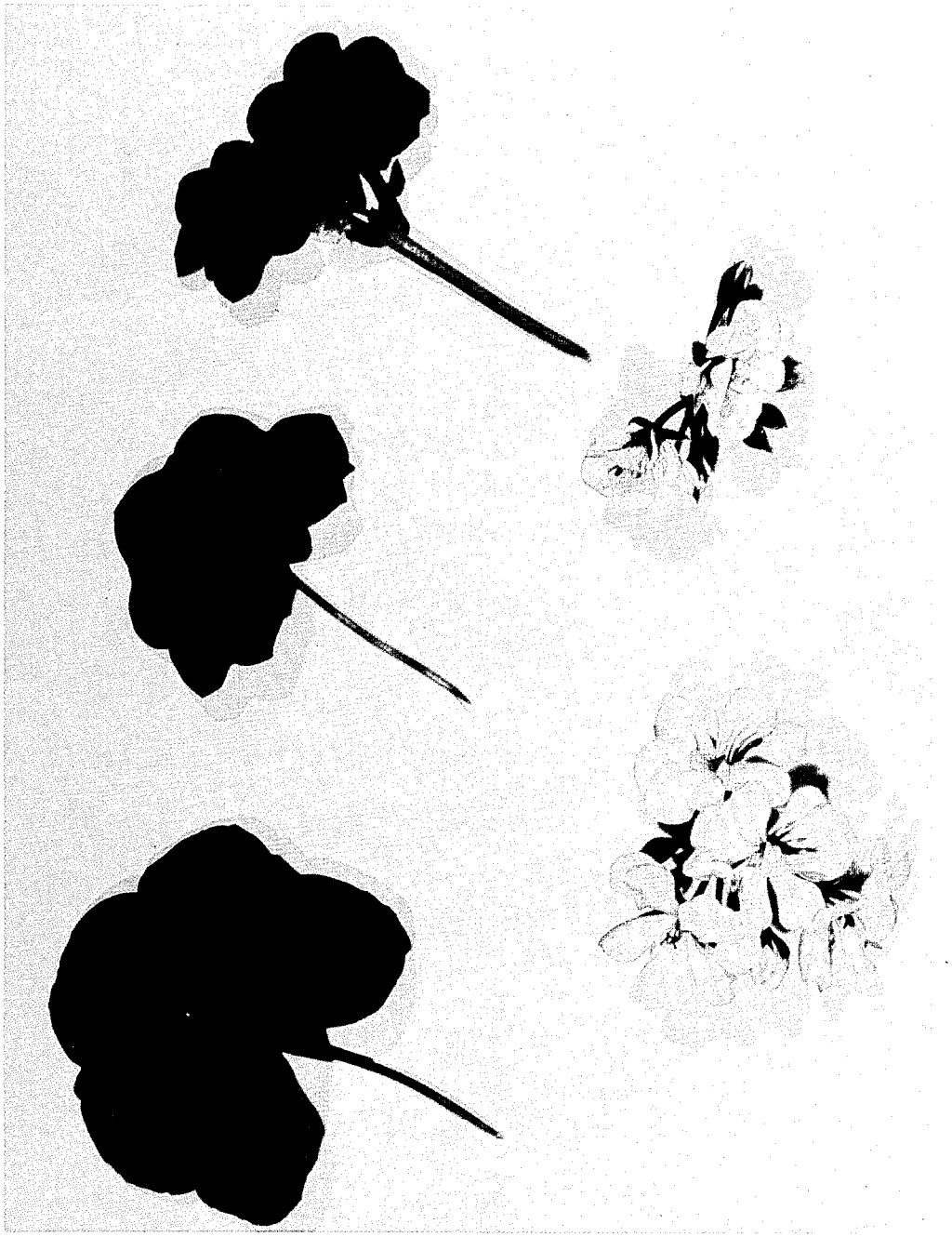

Plant Pat. 3,888

Patented May 18, 1976

1

3,888
GERANIUM PLANT

William E. Duffett, Akron, Ohio, and Walter W. Knicely, Inwood, W. Va., assignors to Yoder Brothers, Barberton, Ohio Filed Mar. 6, 1975, Ser. No. 556,128

Int. Cl. A01h 5/00

U.S. Cl. Plt.—68 1 Claim

The present invention comprises a new and distinct cultivar of *Pelargonium peltatum,* Ait., hereinafter referred to as Cornell (#72120005).

Cornell was originated from a cross made under the supervision of William E. Duffett and Walter W. Knicely in a controlled breeding program in Barberton, Ohio, in the year 1971.

The male, or pollen parent, was Cayucas (unpatented, commercially available), an ivy geranium of fuchsia pink color of unknow parentage.

The female, or seed parent, was Comtesse de Grey (unpatented, commercially available), an ivy geranium of light pink color which was a sport of Mexican Beauty (unpatented, commercially available), an ivy geranium of crimson red color of unknown parentage.

Cornell was discovered and selected as a flowering seedling within the progeny of the stated cross by William E. Duffett and Walter W. Knicely on Aug. 17, 1972, in a controlled environment in Barberton, Ohio.

Cornell is a product of a planned breeding program which had the objective of creating an ivy geranium that would fulfill in part or in whole the need for intensified lavender flower color, increased color retention and increased tolerance of Ohio light and temperature for continuous outdoor summer flowering.

The first act of asexual reproduction of Cornell was accomplished when vegetative cuttings were taken from the initial seedling in September 1972, in a controlled environment in Barberton, Ohio, by a technician according to formulations established and supervised by William E. Duffett and Walter W. Knicely.

Continued asexual reproduction by vegetative cuttings for evaluative tests in flowering and stock programs in conjunction with horticultural certification initiated June 18, 1973, at Barberton, Ohio, have demonstrated that the combination of characteristics as herein disclosed for Cornell are firmly fixed and are retained through successive generations of asexual reproduction.

The following descriptive observations, measurements, and comparisons were derived from plants grown both in a greenhouse and under outdoor conditions. The greenhouse-grown, spring flowered, containerized plants were moved to an outdoor lath area in late May, early June and observed during the summer and fall months. The environmental conditions under which the plants were grown closely approximate those generally used in commercial practice and are described in Chart A and Chart B.

The following traits have been repeatedly observed and are determined to be basic characteristics of Cornell which in combination distinguish this ivy geranium as a new and distinct cultivar:

(1) Medium lavender flower color with minimal color oxidation.

(2) Prolific flowering traits under outdoor summer conditions in Ohio.

(3) Medium green glossy foliage.

(4) Compact spreading growth with medium internode length.

(5) Good foliage durability with minimal breakdown under outdoor summer conditions in Ohio.

2

The accompanying colored photographic drawings show typical flower and foliage characteristics of Cornell. Sheet 1 comprises a photograph of Cornell in bloom, and sheet 2 comprises a photograph showing the development of the inflorescence and the foliage of Cornell. It is noted that difficulty was encountered in obtaining photographs accurately representing the true colors of Cornell. The actual flower color of Cornell is closely approximated in sheet 1. However, the foliage color in both sheets 1 and 2 is not true. The color readings are, however, correct.

The phenotype of Cornell may vary significantly with variations in environment such as temperature, light intensity, and daylength outside the ranges described in Chart A and Chart B. The genotype of Cornell was not observed under all possible environments.

Of the many commercial cultivars known to the present inventors, the most similar existing cultivars in comparison to Cornell are La France (unpatented), and the paternal cultivars Comtesse de Grey and Cayucas. Reference is made to attached Chart C which compares certain characteristics of the above mentioned cultivars with the same characteristics of Cornell. General comparisons are as follows:

(1) In comparison to La France, Cornell has more intense lavender flower color oxidation, more compact (less trailing) growth habit, shorter internode length, more prolific outdoor summer flowering traits and better outdoor summer foliage durability. The general flower color tonality and the flower form of Cornell are similar to those of La France.

(2) In comparison to Comtesse de Grey, Cornell has medium lavender flower color, more compact (less trailing) growth habit, shorter internode length, and more prolific flowering traits under outdoor summer conditions. The flower form and the foliage durability under outdoor summer conditions of Cornell are the same as those of Comtesse de Grey.

(3) In comparison to Cayucas, Cornell has medium lavender flower color and more prolific flowering traits under outdoor summer conditions. The growth habit, internode length, flower form and foliage durability under outdoor summer conditions of Cornell are similar to those of Cayucas.

In the following description, all color references are to the Munsell Limit Color Cascade, 1972 edition. The notation (a) indicates that the color values were determined between 2:00 p.m. and 2:30 p.m. on June 7, 1974, under 150 foot candle light intensity at Barberton, Ohio. The notation (b) indicates that the color values were determined between 2:00 p.m. and 2:30 p.m. on July 22, 1974, under 150 foot candle light intensity at Barberton, Ohio, and the notation (c) indicates that color values were determined between 1:00 p.m. and 1:30 p.m. on Sept. 30, 1974, under 25 foot candle light intensity at Barberton, Ohio.

*Botanical classification: Pelargonium peltatum,* Ait., cv Cornell.

I. Inflorescence

A. Umbel:

*Average diameter.*—3.5 inches.

*Peduncle.*—Ranges from 2 inches to 3.5 inches in length, averaging 2.75 inches.

*Pedicel.*—0.75 inches to 1.25 inches in length, averaging 1 inch.

B. Corolla:

*Average diameter.*—1.8 inches.

CHART A—ENVIRONMENT FOR IVY GERANIUM PERFORMANCE EVALUATION COMMONLY USED IN BARBERTON, OHIO

| | Environment | |
|---|---|---|
| | I. Greenhouse | II. Outdoor lath (30% light reduction) |
| Peiod of Year | February through May | June through September |
| Temperature (°F.) | Night—62–65; Bright day—72–75; Cloudy day—68–70 | Uncontrolled dependent on prevailing weather conditions. |
| Light | Uncontrolled dependent upon natural daylength and light intensity (see Chart B). Light shade compound on greenhouse glass. | Uncontrolled dependent upon natural daylength and light intensity (see Chart B). 30% intensity reduction from lath. |
| Schedule and specifications. | Take vegetative cutting—February 19. Cutting specification—2–2.75 inches in length. Direct stick—February 20; 5 cuttings per 10 inch basket. Media—1 part soil, 1 part peat, 1 part perlite. Pinch—every 4 nodes to finish April 10. Flower—May 28. | Move to outdoor lath location—early June (product produced in I). |

*Type.*—Semi-double; rotate.

| Color: | Spring (a) | Summer (b) |
|---|---|---|
| *Abaxial* | 46–6 | 46–6 |
| *Adaxial* | 46–3 | 46–4 |
| *Blotch* | 46–16 | 46–16 |

C. Bud:

*Shape.*—conodial.

| Color: | Spring (a) | Summer (b) |
|---|---|---|
| *Abaxial* | 46–6 | 46–6 |
| *Adaxial* | 46–3 | 46–4 |
| *Blotch* | 46–16 | 46–16 |

D. Reproductive organs:

*Androecium.* — Stamen: Monodelphous; dorsifixed. Pollen: Present.

*Gynoecium.*—Stigma: 5-lobed; linear. Carpel: 5 locules; pubescent.

E. Response period: Early.

F. Production: Good.

| Date: | *Average number of flowers* |
|---|---|
| July 15, 1974 | 25 |
| Aug. 1, 1974 | 23 |
| Aug. 15, 1974 | 30 |
| Sept. 1, 1974 | 27 |

G. Durability:

*Shatter resistance.*—Poor.

*Tolerance of botrytis.*—Good.

CHART B

INTENSITY OF DIRECT SOLAR RADIATION

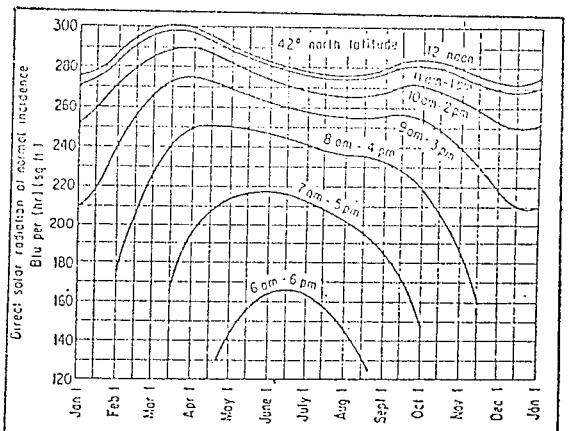

Figure 14.14 Intensity of direct solar radiation normal to the sun's rays at 42 degrees north latitude for an atmospheric clearness number of unity. (Reprinted by permission from *ASHAE Trans.*, Vol. 64, p. 64.)

CHART C—COMPARISON OF CORNELL WITH LA FRANCE COMTESSE DE GREY AND CAYUCAS

| Cultivar | Flower color | Growth habit | Internode length | Outdoor flowering traits | Flower form | Outdoor foliage durability |
|---|---|---|---|---|---|---|
| Cornell | Medium lavender | Compact and spreading | Medium | Excellent | Semi-double | Good. |
| La France | Light lavender | Vigorous and trailing | Long | Good | do | Fair. |
| Comtesse de Grey | Light pink | do | do | Fair | do | Good. |
| Cayucas | Fuchsia pink | Compact and spreading | Medium | do | do | Do. |

NOTE.—Comparisons made of plants grown in a greenhouse and under outdoor lath in Barberton, Ohio under conditions described in Chart A and Chart B.

II. Plant

A. Foliage:

*Form.*—Reniform.

*Margin.*—Undulate.

*Color* (c).—Abaxial: 21–14 to 21–15. Adaxial: 21–12 overlaid with white.

*Durability* (outdoor).—Good.

B. Growth habit:

*Form.*—Spreading.

*Height.*—Compact.

*Internode length.*—Medium.

C. Durability:

*Tolerance of botrytis.*—Good.

We claim:

1. A new and distinct cultivar of geranium characterized particularly by its medium lavender flower color with minimal color oxidation, prolific flowering traits under outdoor summer conditions in Ohio, medium green glossy foliage, compact spreading growth with medium internode length, and by its good foliage durability with minimal breakdown under outdoor summer conditions in Ohio.

No references cited.

ROBERT E. BAGWILL, Primary Examiner